Figure 1A:
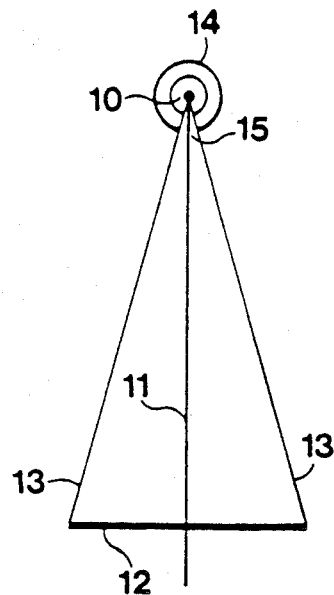

United States Patent [19]
Lundgren et al.

[11] Patent Number: 4,930,143
[45] Date of Patent: May 29, 1990

[54] METHOD AND DEVICE FOR MAMMOGRAPHIC STEREOTACTIC PUNCTION OF PATHOLOGICAL LESIONS IN THE FEMALE BREAST

[76] Inventors: Bengt Lundgren, Norra Ringvägen 23, S-803 57 Gävle; Anders Wallner, Skvattramsvägen 17, S-803 62 Gävle, both of Sweden

[21] Appl. No.: 199,033
[22] PCT Filed: Sep. 21, 1987
[86] PCT No.: PCT/SE87/00423
 § 371 Date: Jul. 13, 1988
 § 102(e) Date: Jul. 13, 1988
[87] PCT Pub. No.: WO88/01847
 PCT Pub. Date: Mar. 24, 1988

[30] Foreign Application Priority Data
Sep. 19, 1986 [SE] Sweden .................................. 8603965

[51] Int. Cl.$^5$ .............................................. A61B 6/04
[52] U.S. Cl. ...................................... 378/37; 128/653 R
[58] Field of Search ...................... 364/413.1, 413.14; 378/37, 10; 128/664, 665, 915, 653

[56] References Cited

U.S. PATENT DOCUMENTS

| | | | |
|---|---|---|---|
| 4,203,037 | 5/1980 | Gur et al. | 378/37 |
| 4,259,585 | 3/1981 | Novak et al. | 378/37 |
| 4,287,425 | 9/1981 | Elliot, Jr. | 378/10 |
| 4,563,768 | 1/1986 | Read et al. | 378/37 |
| 4,599,738 | 7/1986 | Panetta et al. | 378/37 |
| 4,727,565 | 2/1988 | Ericson | 378/37 |
| 4,730,350 | 3/1988 | Albert | 378/10 |

Primary Examiner—Lee S. Cohen
Assistant Examiner—Kennedy J. Schaetzle
Attorney, Agent, or Firm—Larson and Taylor

[57] ABSTRACT

Method and apparatus for stereotactic localization of cancer suspect lesions of the female breast in connection with X-ray mammography. The object is imaged in two directions, and the position of the lesions is calculated from the parallax displacement between the two images. The X-ray tube and the film are held stationary, and the parallax displacement is effected by moving the object laterally.

4 Claims, 11 Drawing Sheets

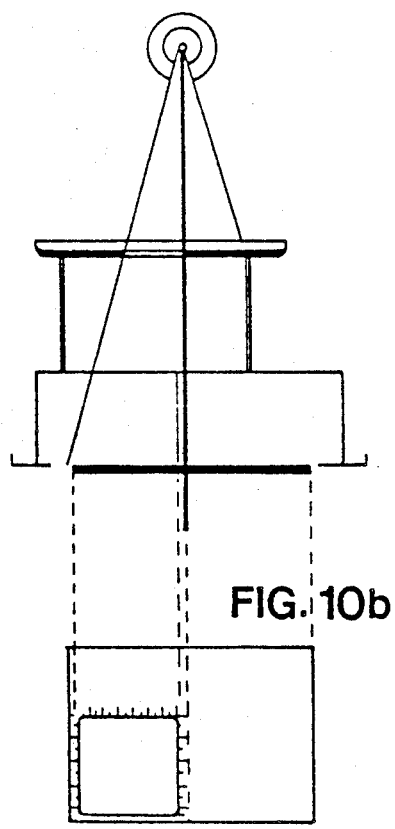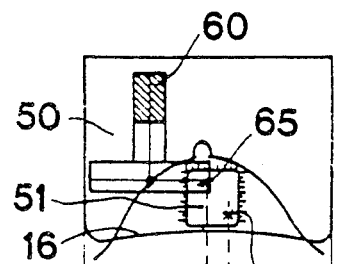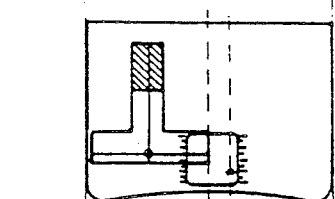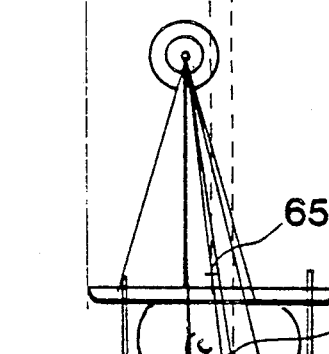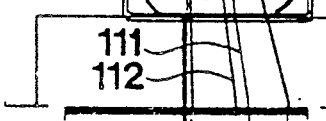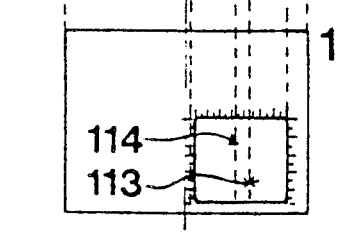

FIG. 14a
FIG. 15
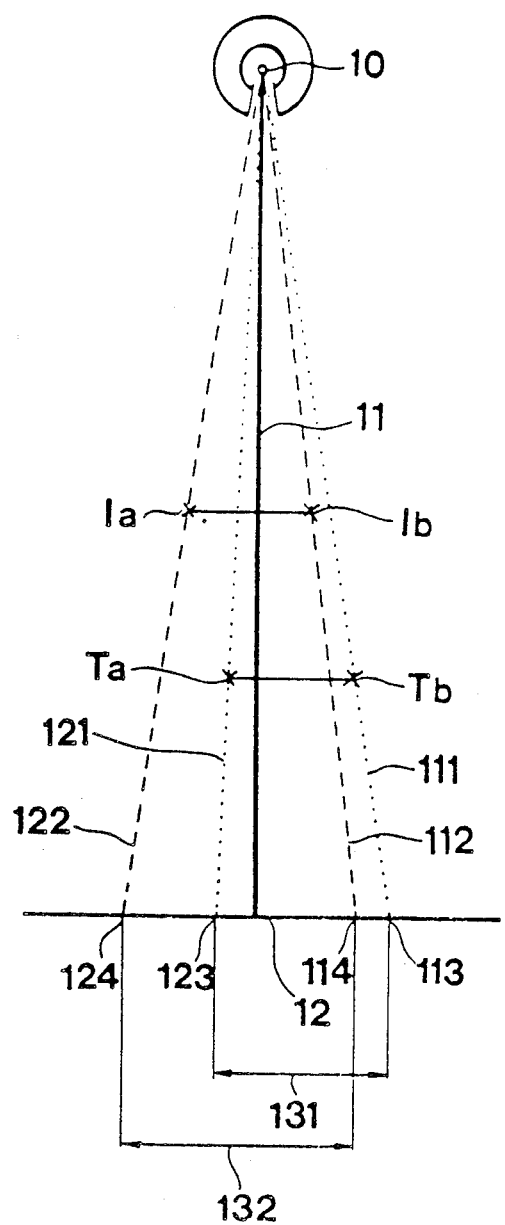
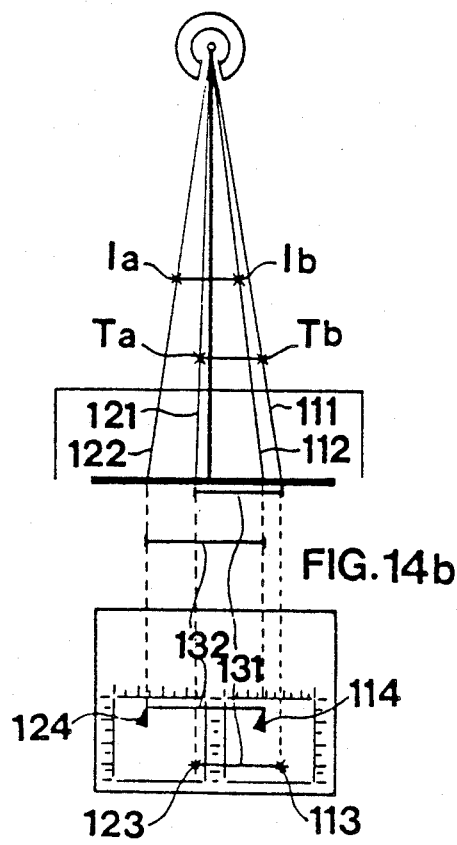

METHOD AND DEVICE FOR MAMMOGRAPHIC STEREOTACTIC PUNCTION OF PATHOLOGICAL LESIONS IN THE FEMALE BREAST

Mammography is a radiographic method for early detection of breast cancer. It is not always possible to decide whether the detected lesions are benign or malignant. One way to decide this is punction with a thin cannula in order to extract cells for microscopic diagnosis. In order to succeed it is necessary to hit the lesions with the cannula. The suspicious lesions are often so small that they can not be palpated (felt with the fingers) and therefore some technique for mammographic localization is necessary.

Mammographic apparatus at present available comprises special versions for the said purpose with stereotactic localization facilities. These imply an extensive modification of the apparatus and raise the price with about 250,000 Swedish crowns. The stereotactic principle (tomography) traditionally used in radiology is based on the object being stationary and the X-ray tube (radiation source) and film cassette (image medium) moving synchronously. Two exposures are made and with the aid of simple geometry it is possible to calculate the position within the object. Such equipment is technically complicated and therefor expensive, especially since it is usually combined with relatively sophisticated computerization.

The present invention suggests a principle that is the reverse of the above and not previously used in radiological technique, i.e. to allow the X-ray tube and the image to remain stationary and to move the object. As a consequence, the X-ray unit need not be modified. The geometry in this case is also simple, being based on similar triangles. There is, however, requested an apparatus having a movable holder adapted to hold the object—the female breast—during the movement between the two positions of exposure. The invention can be adapted to all existing mammography units without having to modify these.

The invention is described in the following specification, and the accompanying drawings show:

FIGS. 1a and b, the principle for a conventional standard mammography unit without stereographic means.

Figure 2A:
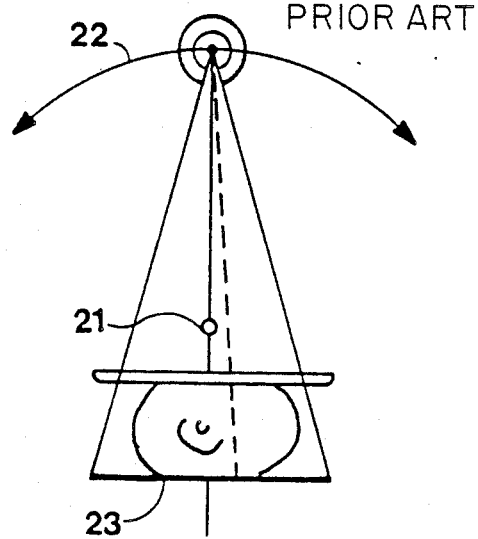
Figure 2B:
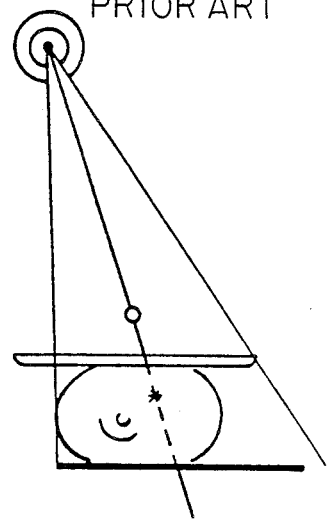
Figure 2C:
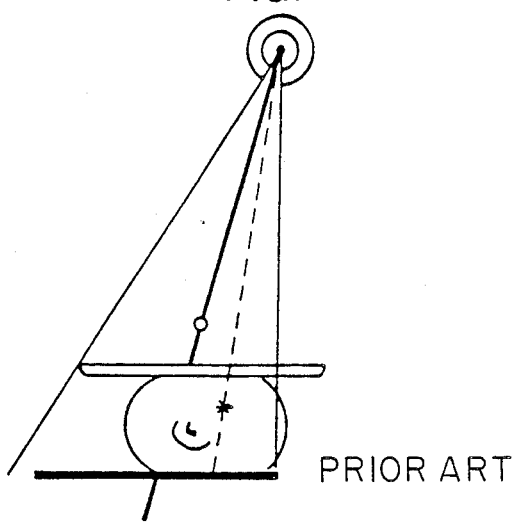

FIGS. 2a to c, a conventional X-ray unit with stereographic means.

FIGS. 3 to 7 show various details of the present invention.

Figure 4:
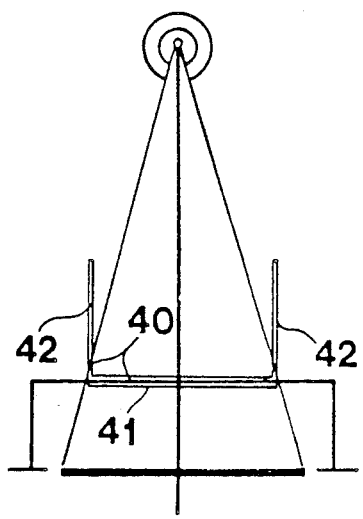

FIG. 4, an object holder on the stand.

Figure 5A:
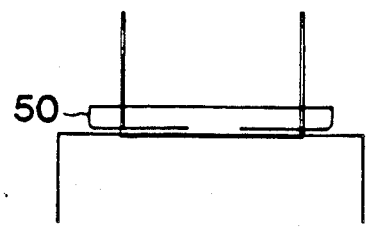
Figure 5B:
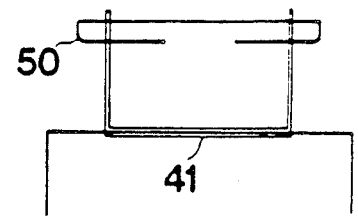

FIG. 5, a compression plate on the object holder.

Figure 6A:
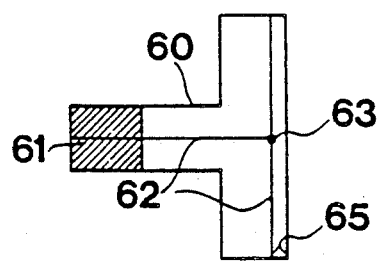
Figure 7:
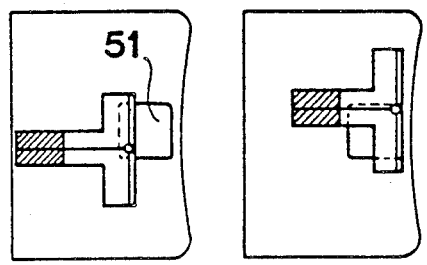

FIGS. 6a and b and FIG. 7, a needle director on the compression plate.

Figure 8:
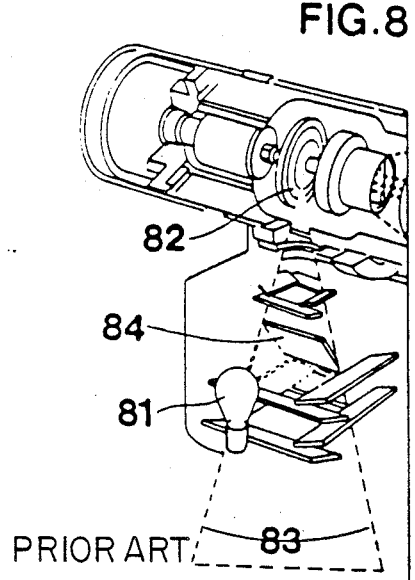

FIG. 8, a perspective view of devices for X-ray tube and light source.

FIGS. 9 and 10, different functions of the invention.

Figure 9A:
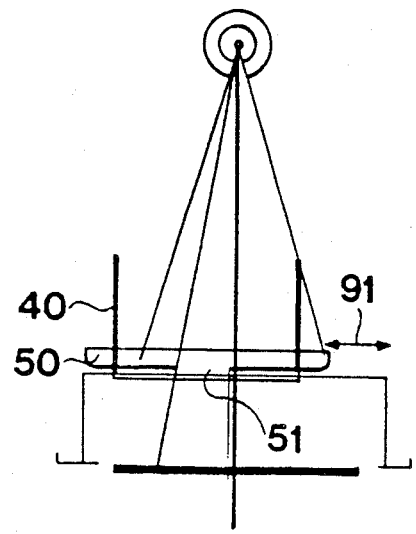

FIGS. 9a and b, lateral movement of object holder.

FIGS. 10a and b, vertical movement of compression plate.

FIGS. 11 to 13, handling of unit according to the present invention.

FIGS. 11a to d, the principle for exposure.

Figure 12A:
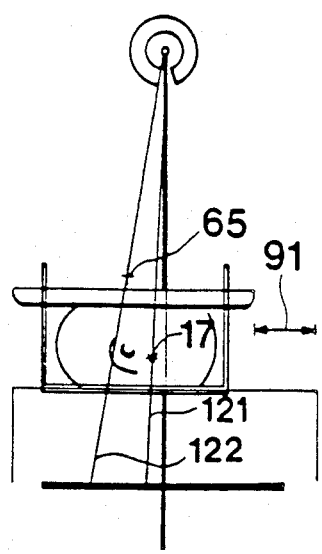

FIGS. 12a and b, exposure in the two outer positions.

Figure 13A:
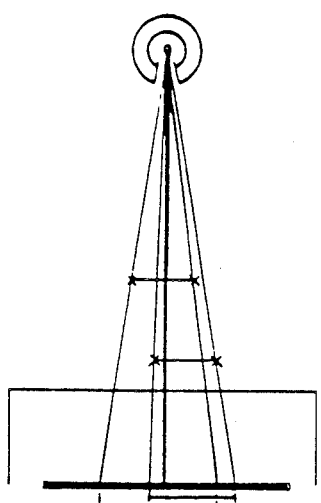

FIGS. 13a and b, the exposures put together.

FIGS. 14 to 18, the mathematical basis for calculation of the depth of punction.

Figure 19:
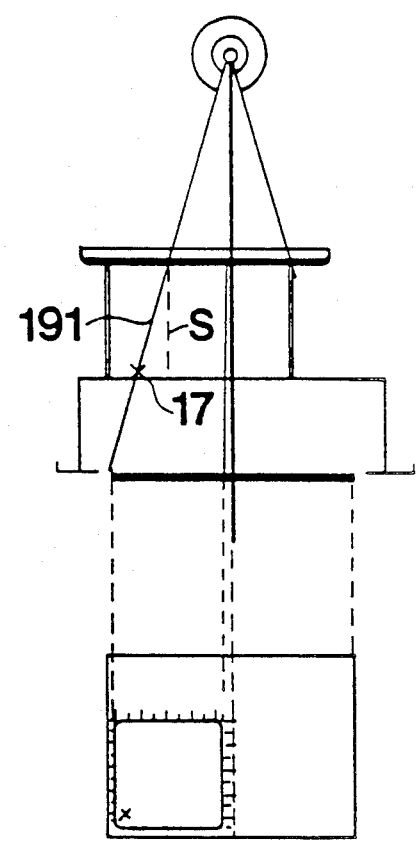

FIG. 19, illustration of direction of punction.

CONVENTIONAL MAMMOGRAPHY

The principle for a conventional mammography unit without stereographic means is shown in FIGS. 1a and b. The X-ray tube 10 is mounted on a stand 11 which is immovable in relation to the film cassette holder 12. The outer limits of the radiation field from the X-ray tube are schematically shown by the continuous lines 13. The primary diaphragm 14 of the X-ray tube and the radiation window 15 decide the size of the radiation field.

Figure 1B:
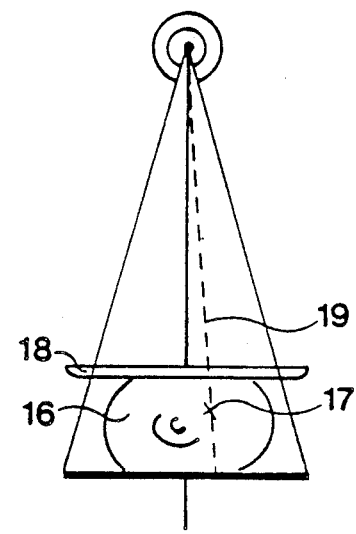

FIG. 1b shows the object 16, a female breast, with the suspicious lesion 17. The object is fixed by a compression plate 18 on top of the film cassette, also fixed. The X-ray beam passing through the lesion is shown by a broken line 19.

TOMOGRAPHY

FIGS. 2a to c show a conventional X-ray unit with stereographic means for tomography. The X-ray tube is mounted on a stand which is movable around an axis 21. The movement limits of the X-ray tube are delineated by line 22. The stand is mechanically fixed to the film cassette holder 23, which will move accordingly in a direction opposite to the X-ray tube. FIGS. 2b and c show exposures in the two extreme positions. As mentioned the unit is technically advanced and thus expensive.

MOVEMENT OF THE OBJECT

The method and device according to the present invention are presented in the following descriptions and figures of principle. The device may be used on presently existing mammography units without modification of the latter. The device consists of four main components, i.e. base, object holder, compression plate and needle director.

BASE

Figure 3:
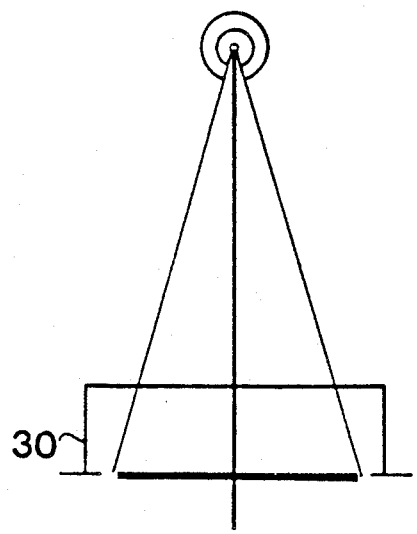

FIG. 3 shows a base 30 which is attached in connection with the cassette holder of an existing mammography unit. The base has two functions:
1. It allows for magnification of the image by increasing the object-film distance.
2. It acts as a slide track for lateral movements of the object holder 40 (see FIG. 4).

OBJECT HOLDER

FIG. 4 shows the object holder 40 mounted on the base. The object holder has a base plate 41 on which the object (the breast) rests. The object holder has also a stand 42, allowing for vertical movement of the compression plate 50 (see FIG. 5). The object holder can be moved laterally in relation to the base between two fixed extreme positions. The length of the lateral movement is known and constant.

COMPRESSION PLATE

The compression plate 50 is mounted on the object holder. The compression plate is movable in the vertical direction as shown in FIGS. 5a and b. The object is held in a locked position between the compression plate and the base plate 41.

Figure 5C:
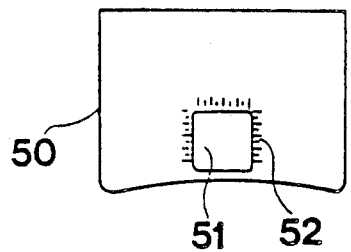

FIG. 5c shows the compression plate as viewed from above. In the fore middle part of the compression plate there is a hold 51 which is 5 cm by 5 cm and allows the passage of X-radiation for film exposure and later is used for punction.

The rest of the plate is covered by a thin iron sheet, the function of which is to:
1. serve as a secondary diaphragm, reducing the size of the irradiated field of the breast and the patient to only 25 cm².
2. serve as a receptor for the needle director 60 which is provided with a magnet (see FIG. 6).

Around the hole 51 there are markings 52. They are cut out in the iron sheet and let thus through the X-rays which accordingly are visible on the exposed X-ray film. The markings are used for deciding the x and y coordinates when performing the punction (see below).

NEEDLE DIRECTOR

Figure 6B:
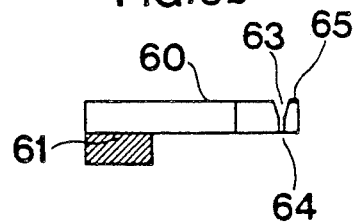

FIGS. 6a and b are drawn at twice the scale of the previous figures. FIG. 6a shows the principle for the needle director 60 as viewed from above, while FIG. 6b shows a view from the side. The needle director is made of clear plastic and is held in position on the compression plate by magnets 61 at the rear end of the needle director which thus can be moved along the upper surface of the compression plate. On the upper side of the needle director are two marking 62 lines at right angles. These marking lines 62 will cast a shadow when lighted by a common light-bulb. The markings form a hair-line cross and an origin 63 with a steering hole 64 for the punction cannula.

Before punction the origin 63 is adjusted to the determined xy-coordinate with the aid of the light diaphragm 81 (see FIG. 8). Concerning punction see below under "Operation".

FIG. 7 shows that the needle director is constructed to enable the origin 63 to be set to all xy-coordinates within the hole 51.

On one of the corners of the needle director there is attached a very thin lead (Pb) indicator 65. On exposures this indicator is positioned within the radiation beam, limited by the hole 51. By this procedure the displacement of the position of the indicator 65 on the X-ray film can be measured directly, which substantially facilitates the calculation of the level of the lesion.

FIG. 8 is taken from a leaflet from Siemens on X-ray light diaphragms. The X-ray radiation source, the anode 82, emits the X-ray beam marked with the dashed lines 83. The X-rays pass without deviation through a mirror 84. In connection with the X-ray tube there is also a light bulb, a so called light diaphragm 81, the beam of which will be directionally identical to the X-ray beam.

FUNCTION

FIGS. 9a and b show the lateral movement of the object holder 40. The movement is between two fixed extreme positions and the movement distance 91 is thus known. The X-ray beam is shadowed in the figure and as the figures show the radiation is allowed to pass only through the hole 51 of 5×5 cm² size in the compression plate 50. By this procedure only half of the film medium will be used per exposure, while the other half is screened from radiation. The two images will be exposed on the same film.

Figure 9B:
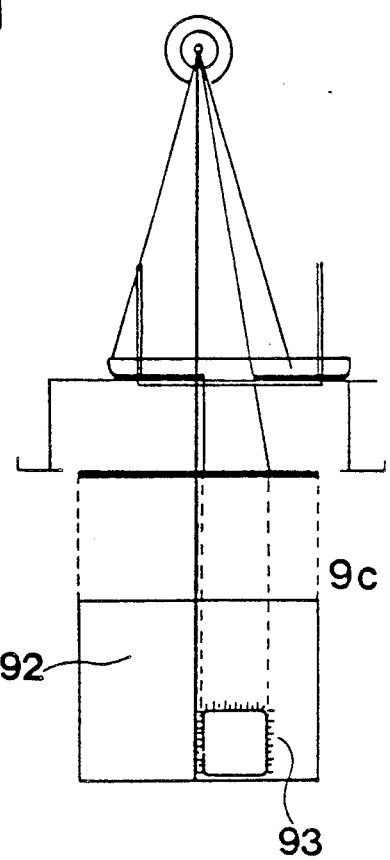

FIGS. 9a and 9b are drawn with the compression plate in its bottom position.

FIG. 9c shows the X-ray film 92 after one exposure with the object holder in the right extreme position according to FIG. 9b. As shown in FIG. 9c, only the right half of the film will be exposed. Without changing film the object holder can now be moved to the left extreme position, as is shown in FIG. 9a, and the second exposure is made, thus allowing the left half of the film to be used for this exposure. FIG. 9c also shows how the millimeter markings 52 on the compression plate are seen at 93 on the exposed X-ray film.

FIG. 10a shows the apparatus in the same position as in FIG. 9a, however the difference being that the compression plate is moved vertically to its top position (in reality 8 cm). Otherwise the conditions are the same as in FIG. 9a. FIG. 10b shows the X-ray film after an exposure with a setting as in FIG. 10a. As shown in FIG. 10b only the left half of the film is exposed. On comparing with FIG. 9c the exposed part of the film is larger. Exposing as in FIG. 10a results in exposing the left half of the film from the middle line to the outer edge.

OPERATION

With the aid of a previously made complete mammographic examination the suspicious lesion area 17 in the breast 16 is positioned within the image field, which is limited by the square hole 51 in the compression plate 50. In the image field is placed also the lead (Pb) indicator 65.

In FIG. 11a the compression plate is transparent for didactic reasons. FIG. 11a is viewed from above. The object (the breast) 16 is compressed by the compression plate 50. In the hole 51 the suspicious lesion 17 is placed. The needle director 60 is placed so that the indicator 65 lies within the image field. FIG. 11b shows the same as 11a with the difference that the compression plate is X-ray opaque.

FIG. 11c shows the same situation as viewed from the front. The object holder is in the right extreme position. The X-ray beams passing through the indicator 65 and the lesion 17 are marked with lines 112 and 111 respectively. The X-ray field is shaded as in FIG. 9b. FIG. 11d shows the exposed film in accordance with FIG. 11c. On the film the images of the lesion 113 and the indicator 114 are shown.

Figure 12B:
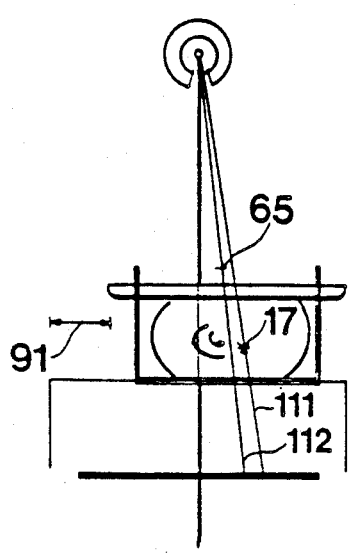

FIGS. 12a and 12b show the practical operation. After placing the suspicious lesion 17 and the indicator 65 within the image field, as shown in FIG. 11, the first exposure is made in one extreme position. The object holder is then moved to the opposite extreme position while retaining the fixation of the breast, and a second exposure is made on the same film. The lateral movement 91 (referred to below as $D_F$) is in reality only 8 centimeters, and clinical tests have shown that the lateral movement can be performed without problems and without disturbing the fixation of the breast.

FIG. 12a shows the exposure with the object holder in the left position with only significant rays being marked in the figure, i.e. the one through the lesion 121 and through the indicator 122. FIG. 12b shows the corresponding situation in the right position, with X-rays 111 through the lesion and 112 through the indicator.

Figure 13B:
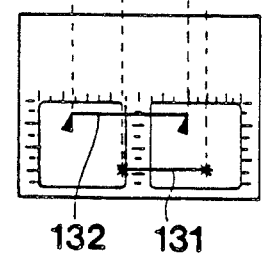

FIG. 13a shows the significant rays at exposures according to FIGS. 12a and 12b (compare also FIGS. 14 to 19). FIG. 13b shows the X-ray film after the two exposures.

Figure 13C:
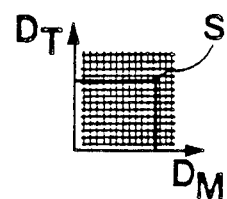

The patient remains sitting with the breast under fixation, while the film cassette is removed and the film processed. The distances 131 ($D_T$) and 132 ($D_I$) are measured directly on the film. The penetration depth S from the steering hole 64 of the cannula director to the lesion can thereafter be directly read from a table which is based on the calculations below (FIG. 13c). The penetration depth is marked on the punction cannula with a sterile plastic tube of the correct length. By means of the last image exposed the x-y-coordinates are determined. (In this case the righthand picture, corresponding to FIG. 12b).

The apparatus remains in the same position as for the last exposure, and the breast is still fixed. With the aid of the mm-markings 52 on the compression plate the hairline cross 62 on the cannula director is set to the correct x-y-coordinate in the light of the light diaphragm 81. The punction is then performed through the steering hole 64 in the direction of the light from the diaphragm to the correct depth, which thus is marked on the cannula.

The whole procedure inclusive film developing, measuring and setting the penetration depth, measuring and setting x-y-coordinates etc takes only a few minutes, and the patient has no problem remaining seated with her breast fixed in the object holder during this time.

MATHEMATICAL BACKGROUND

In FIGS. 14a and 14b the aspects of FIGS. 12 and 13 have been combined and completed with symbols. The factual positions (marked x) of the lesion 17 have been called Ta and Tb respectively, while the factual positions of the indicator have been called Ia and Ib respectively. Rays are marked as in the previous figures.

FIG. 14b shows the X-ray film after both exposures as described in FIG. 12. In FIG. 12b the circumstances are identical with FIG. 11d, and on the film the lesion 113 and indicator 114 are imaged as in the right part of FIG. 14b. In analogy, the images of the lesion and the indicator in the left part of FIG. 14b are called 123 and 124 respectively. The distance between the images of the lesion is called 131 (in the equations below $D_T$) and the distance between the images of the indicator is called 132 (in the equations below $D_I$). These distances 131 and 132 are measured directly on the film.

FIG. 15 is similar to FIG. 14a, however magnified to twice the size, and the designations are as in the previous figures. The basis for calculations is the geometry of similar triangles. The following symbols are used in the equations and calculations:

$H_T$=level of focus over the lesion
$H_I$=level of focus over the indicator
$D_T$=distance between the images of the lesion (above called 131)
$D_I$=factual movement of the holder (above called 91). As the lesion and the indicator are moved together with the holder, also their factual movement=$D_F$
FFD=film-focus distance.

Figure 16:
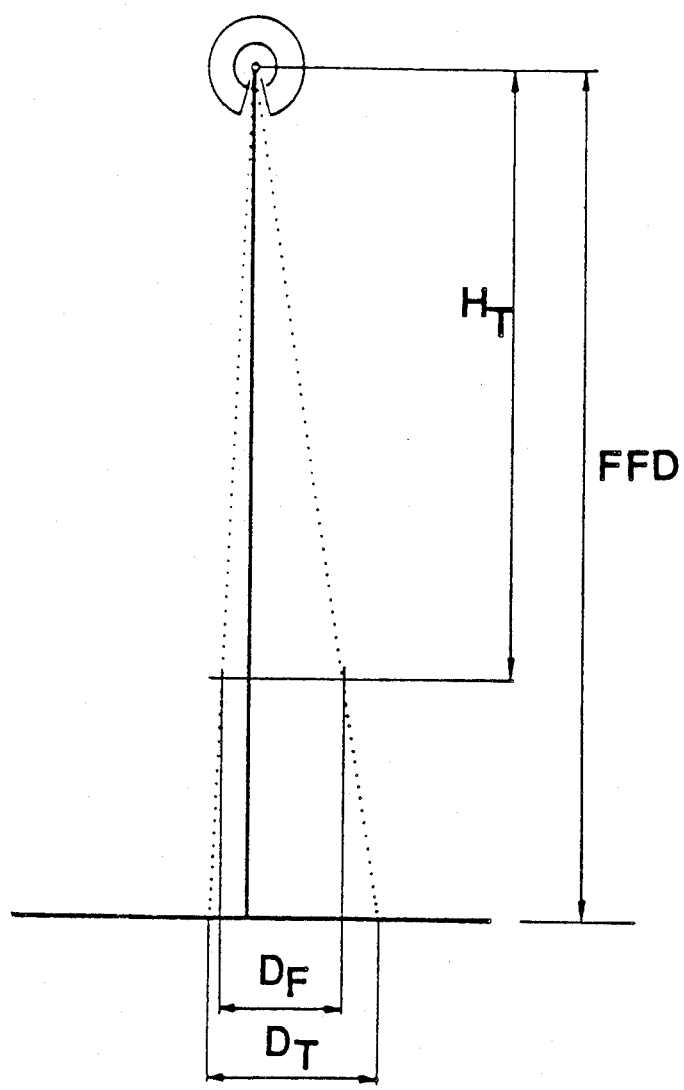

FIG. 16 shows the triangle, also found in FIG. 15, with the corners 10, 113 and 123. According to the law of similar triangles is obtained:

$$\frac{H_T}{D_F} = \frac{FFD}{D_T}$$

$$H_T = \frac{D_F \cdot FFD}{D_T}$$

Figure 17:
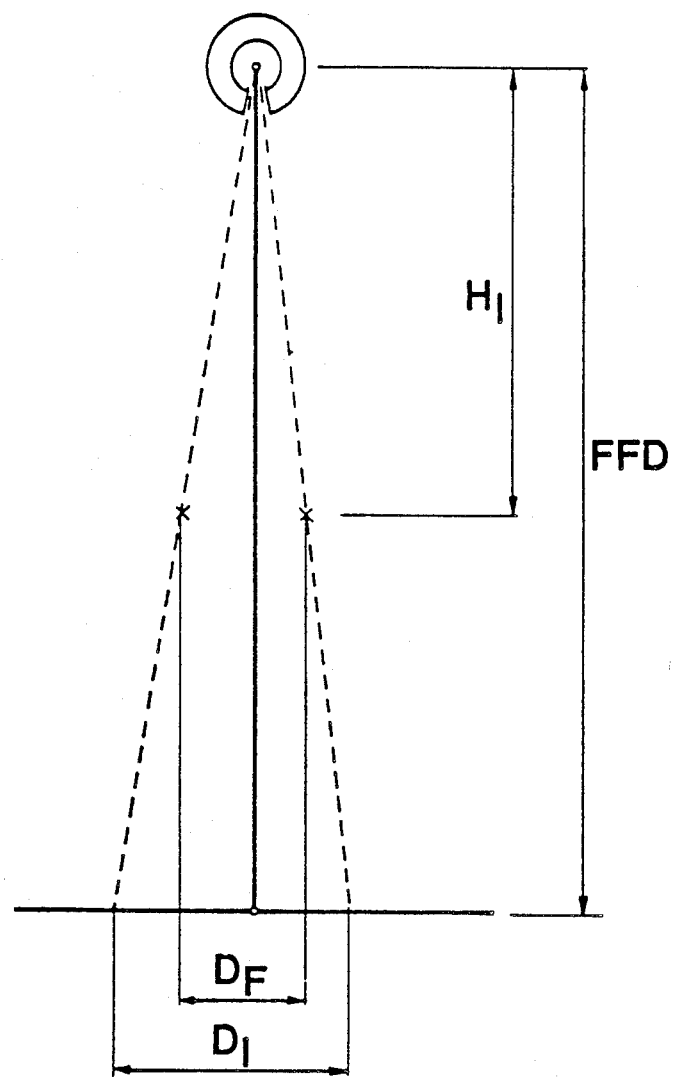
Figure 18:
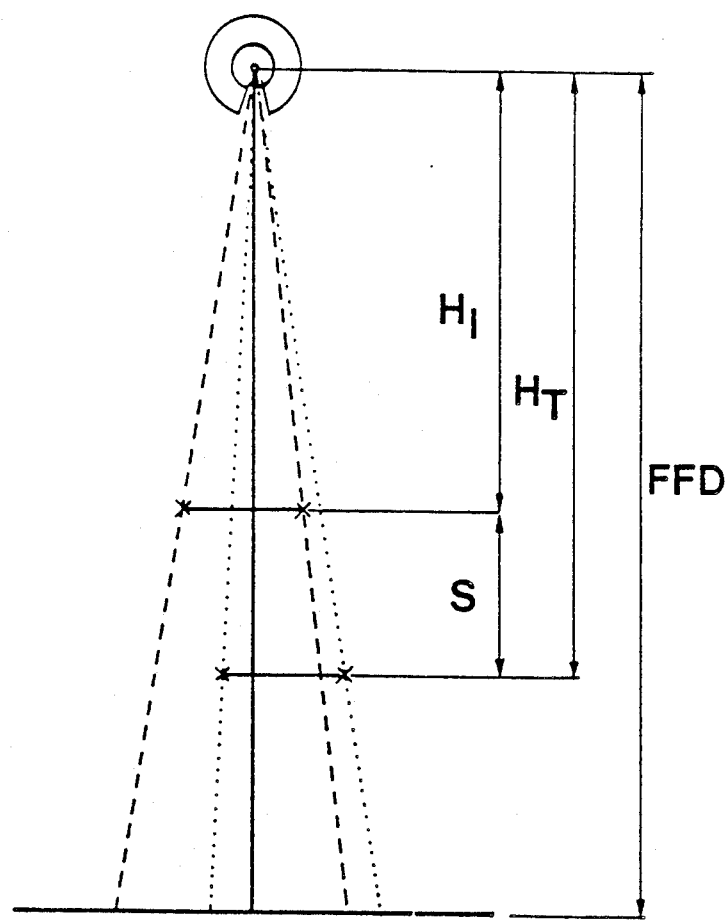

FIG. 17 shows the triangle, also found in FIG. 15, with the corners 10, 114 and 124. In analogy with FIG. 16 is obtained:

$$\frac{H_I}{D_F} = \frac{FFD}{D_I}$$

$$H_I = \frac{D_F \cdot FFD}{D_I}$$

The important distance is the one between the levels of indicator and lesion, which below is called S. It follows from FIG. 18 that $$S = H_T - H_I$$

in which equation the above obtained expressions for $H_T$ and $H_I$ are substituted:

$$S = \frac{D_F \cdot FFD}{D_T} - \frac{D_F \cdot FFD}{D_I}$$

$$S = D_F \cdot FFD \left( \frac{1}{D_T} - \frac{1}{D_I} \right)$$

FFD is a known figure for any X-ray unit. $D_F$ is also known. These two figures can thus be combined to a constant K, specific for the apparatus.

$$S = K \cdot \left( \frac{1}{D_T} - \frac{1}{D_I} \right)$$

It can be noted that the punction is not made perpendicularly to the compression plate but in the direction of the beam from the light diaphragm. The punction channel is the hypotenuse in a 90 degree triangle in which the altitude is S. There is thus a slight discrepancy between the calculated S and the factual punction depth. FIG. 19 shows a lesion 17 and the 90 degree triangle in which the direction of the beam through the lesion is the hypotenuse 191 and the altitude S is the calculated punction depth.

The circumstances for punction in FIG. 19 are at maximum disadvantage, due to a maximum distance between the compression plate and the base plate combined with a lesion situated near the base plate and near the edge of the image field. In such a case the difference between S and the punction channel (hypotenuse) will be <2 millimeters.

This extreme example can easily be avoided by compressing the breast in another direction.

In normal circumstances the difference between S and the hypotenuse is not measurable, and thus clinically insignificant.

We claim:
1. A mammographic unit for use in stereographic localisation in a breast of a lesion suspected of being cancerous, said unit comprising:
   a stand;
   an x-ray tube mounted on the stand so as to emit an x-ray beam in a defined field;
   a holder means, laterally slidable with respect to said beam between a first imaging position within said field and a second imaging position within said field, for receiving a breast and for restraining the breast in a fixed shape, the fixed shape being maintained when the holder means is displaced between said first and second positions; and means for holding a film, located within the x-ray field and held stationary relative to the x-ray tube, in a position such that a first picture of said breast taken at the first imaging position and a second picture of the breast taken at the second imaging position will be located side by side on the film.

2. A unit according to claim 1 further comprising an indicator means, mounted on the holder means, for providing x and y coordinates on the film so that the position of a lesion is defined with reference to said x and y coordinates, and a z-coordinate is calculable from displacement of the lesion between the two pictures imaged on said film.

3. A unit according to claim 2 which also comprises, mounted on the holder means,
   a punction cannula, and
   means for steering the punction cannula to the x-y-z coordinates in the breast.

4. A method for stereographic localisation in a breast of a lesion suspected of being cancerous using a mammographic unit comprising an x-ray tube mounted on the stand so as to emit an x-ray beam in a defined field; a holder, laterally slidable, with respect to said beam, between a first imaging position within said field and a second imaging position within said field, for receiving a breast and restraining the breast in a fixed shape, and means for holding a film, located within the x-ray field and held stationary relative to the x-ray tube, in a position such that a first picture of said breast taken at the first imaging position and a second picture of the breast taken at the second imaging position will be located side by side on the film;

said method comprising:
   placing a breast in the holder, and restraining the breast in a fixed shape;
   exposing the breast to x-rays while the holder is in said first imaging position so that a first picture is made on the film;
   sliding the holder to said second imaging position while restraining the breast in the fixed shape thereof;
   exposing the breast to x-rays while the holder is in its second imaging position so that a second picture is made on the film adjacent the first picture;
   using said first and second pictures to calculate the perceived parallactic displacement of a lesion imaged on the film; and
   using said displacement to determine the position of the lesion within the breast.

* * * * *